United States Patent [19]

Barrett

[11] Patent Number: 5,698,200

[45] Date of Patent: Dec. 16, 1997

[54] ANTIMICROBIAL PRODUCT AND PROCESS

[75] Inventor: Karen B. Barrett, Idaho Falls, Id.

[73] Assignee: Lockheed Martin Idaho Technologies Company, Idaho Falls, Id.

[21] Appl. No.: 689,805

[22] Filed: Aug. 14, 1996

[51] Int. Cl.$^6$ .............................. A01N 65/00; A61K 35/78
[52] U.S. Cl. ......................... 424/195.1; 514/783; 536/128; 435/291.1
[58] Field of Search .................... 424/93.2, 93.1, 424/405, 195.1; 435/29, 30, 172.3, 291.1; 514/651, 783; 536/128

[56] References Cited

U.S. PATENT DOCUMENTS

| | | | |
|---|---|---|---|
| 4,939,284 | 7/1990 | Degenhardt | 558/142 |
| 5,273,749 | 12/1993 | Bok et al. | 424/405 |
| 5,288,634 | 2/1994 | Harman et al. | 435/244 |
| 5,409,957 | 4/1995 | Oda et al. | 514/651 |
| 5,422,108 | 6/1995 | Mirkov et al. | 424/94.61 |
| 5,428,146 | 6/1995 | Logemann et al. | 536/24.1 |
| 5,441,735 | 8/1995 | Takahara et al. | 424/93.2 |
| 5,505,940 | 4/1996 | McGuire et al. | 424/93.1 |

*Primary Examiner*—James Ketter
*Assistant Examiner*—Irem Yucel
*Attorney, Agent, or Firm*—Thorpe North & Western

[57] ABSTRACT

A composition for controlling a plant disease caused by a plant pathogenic bacterium is disclosed. The composition comprises an activity for inhibiting the growth of the plant pathogenic bacterium and is extracted in an aqueous solvent from particles of malted cereal grain. The composition is used either in dry or wet form by application to plant parts, such as potato seed pieces, that are to be protected from the pathogenic bacteria.

19 Claims, 6 Drawing Sheets

FIG. 1

Screening
Erwinia carotovora ssp carotovora

Zone of Inhibition by Treatment:
- Steriled H₂O: 0
- Raw: 0
- Whole Kernel: 1.13
- Coarse Grind: 6.1
- Fine Grind: 0
- Cell-Free Fine: 0.1
- Green Malt - 0: 0.1
- Green Malt -3: (not labeled)

ANTIMICROBIAL PRODUCT AND PROCESS

CONTRACTUAL ORIGIN OF THE INVENTION

The United States Government has rights in this invention pursuant to Contract No. DE-AC07-94ID13223 between Lockheed Martin Idaho Technologies Company and the United States Department of Energy.

BACKGROUND OF THE INVENTION

This invention relates to a composition and method for controlling plant diseases. More particularly, the invention relates to a composition prepared from malted cereal grains and a method of use thereof for application to crop plants for controlling plant diseases caused by pathogenic microorganisms.

Plants are exposed to many microbes, including bacteria, viruses, fungi, and nematodes. Although many of the interactions between these microbes and plants are beneficial or innocuous, many of the interactions are harmful to the plants. Diseases of agricultural crops, ornamental plants, forests, and other plants caused by such plant pathogens, particularly bacterial pathogens, are a worldwide problem with enormous economic impact.

There are many pathogenic species of bacteria, fungi, and nematodes. Diseases caused by fungal species include pre- and post-emergence seedling damping off, hypocotyl rots, root rots, crown rots, and the like. Pathogenic nematodes cause diseases such as root galls, root rot, stunting, and various other rots. Some nematodes also function as vectors of plant viruses.

Bacterial pathogens have a significant impact on worldwide agriculture. Such plant pathogenic bacteria include species of *Pseudomonas, Erwinia, Agrobacterium, Xanthomonas*, and *Clavibacter. Pseudomonas* and *Xanthomonas* species affect a large number of different crops. For example, *Pseudomonas syringae* pathovar *tomato* causes bacterial speck of tomato; *Xanthomonas campestris* pv. *malvacearum* causes angular leaf spot of cotton; *Pseudomonas solanacearum* causes bacterial wilt of potato; and *Pseudomonas tolaasii* causes brown blotch disease of cultivated mushrooms. Potatoes and many other crops, such as celery, head lettuce, carrot, Japanese radish, wasabi, tobacco, tomato, cyclamen, Chinese cabbage, and cabbage, are susceptible to the so-called bacterial soft rots.

*Erwinia carotovora* is a soft rot bacterium that softens and rots storage tissues of many plants and is reported to be ubiquitous in soil. The bacterium typically enters plant tissues through injuries caused by insects, wind, tools, and the like. The bacterium invades the site of injury, and if temperature and moisture conditions are suitable, the bacteria rapidly multiply and macerate the tissue. For example, *Erwinia* bacteria are latent in potato plants, and will preferentially attack the stem and the tubers only after wounding. Potato seed pieces are also susceptible to infection through the cut surfaces. *Erwinia carotovora* subsp. *carotovora* has a substantial impact on the potato industry.

Agricultural production of major crops has always been impeded by plant pathogens. Diseases caused by plant pathogens often limit the growth of certain crops to certain geographic locations and can destroy entire crops. Crop losses resulting from the deleterious effects of plant pathogens are, thus, a serious worldwide agricultural problem, particularly since there are no known treatments for many of the diseases caused by plant pathogens. Even in instances where agrichemicals and pesticides are effective against plant pathogens, their use is increasingly under attack because of injurious effects on the environment and human health.

Because pesticides are often ineffective, unavailable, and/or environmentally unacceptable, there is a need to develop alternative means for effectively eradicating or reducing the harmful effects of plant pathogens. In recent years, much research has focused on the development of means for biocontrol of such pathogens and on the development of pathogen-resistant plants by breeding or by genetic engineering. There are few examples, however, of successful production of effective biocontrol methods or disease-resistant plants.

Application of antibiotics, such as streptomycin, and metal compounds, such as copper-containing Bordeaux mixture, has been the conventional method of control for many bacterial diseases. For example, *Pseudomonas syringae* pv. *tomato*, which causes bacterial speck of tomato, is presently controlled by frequent application of copper-containing sprays, which, in addition to their unfavorable environmental impact, select for copper-resistant strains. Treatment of apple and pear orchards with streptomycin to control the fireblight pathogen, *Erwinia amylovora*, has resulted in the appearance of streptomycin-resistant strains. *Xanthomonas campestris* pv. *malvacearum*, which causes angular leaf spot of cotton, presently is controlled by treating seeds with mercury-containing compounds and copper sprays. Other *Xanthomonas campestris* species, such as *X. campestris* pv. *vesicatoria* and *X. campestris* pv. *campestris*, can be seedborne, and there are no effective means for treating the seeds without injury thereto. These chemicals give unsatisfactory control, however, and also kill useful bacteria, contaminate the environment, and cause chemical injuries. Antibiotic-resistant bacteria have also appeared, and the ability of bacteria to transfer multiple drug resistance genes between genera potentially threatens antibiotic treatment of diseases of humans and/or animals.

Since there are few means for controlling plant bacterial pathogens, and those that are available, such as the heavy metal-containing sprays and antibiotics, are not highly effective and are environmentally unacceptable, and since there are relatively few bacterial pathogen-resistant vegetable or fruit plants available, there is a need for the development of effective, non-toxic, biodegradable and environmentally acceptable means for the control of plant pathogens. There is also a need to develop means for treating plants to eradicate or control plant diseases of bacterial origin.

M. McGuire et al., U.S. Pat. No. 5,505,940, describe a sprayable gluten-based formulation for pest control wherein solubilized gluten is mixed with a biological or chemical control agent in an aqueous solvent. The gluten disperses the control agent, improves adherence and rainfastness on the surface to which it is applied, and improves longevity of the active agent.

Y. Takahara et al., U.S. Pat. No. 5,441,735, disclose a composition and method for controlling soft rot, bacterial seedling blight of rice, and black rot comprising a mutagenized, nonpathogenic strain of *Erwinia carotovora* subsp. *caratovara* for application to soil or plants in mixture with a chemically synthesized water-soluble high molecular weight compound, polysaccharide, or protein for improving the wettability of the bacterial cells.

J. Logemann et al., U.S. Pat. No. 5,428,146, disclose a DNA sequence stimulated by wounding or attack by a pathogen.

T. E. Mirkov et al., U.S. Pat. No. 5,422,108, describe compositions and methods for treating plants or plant tissues prior to or after exposure or infection with a bacterial plant pathogen comprising a ruminant lysozyme.

M. Oda et al., U.S. Pat. No. 5,409,957, describe a phenoxyalkylamine and salts thereof for killing of certain plant pathogenic bacteria when applied directly to the plant or to the soil or water.

C. R. Degenhardt, U.S. Pat. No. 4,939,284, describes tetraalkyl ethenylidenebisphosphonate esters suitable as antimicrobial agents for combatting pathogenic microorganisms.

S. H. Bok et al., U.S. Pat. No. 5,273,749, disclose a process for preparing a coated microbial pesticide comprising antagonistic microorganisms and natural biopolymers. The biopolymers can be derived from grains, tubers, roots, and the like. The biopolymers serve as a source of metabolic nutrients for the antagonistic microorganisms, provide for sustained delivery of the bioactive materials, are highly adhesive, are pollution free, and are inexpensive.

In view of the foregoing, it will be appreciated that providing compositions and methods for controlling plant pathogens, especially pathogenic bacteria, wherein such compositions and methods are effective, inexpensive, and environmentally friendly, would be a significant advancement in the art.

BRIEF SUMMARY OF THE INVENTION

It is an object of the present invention to provide compositions and methods for controlling plant diseases.

It is also an object of the invention to provide compositions and methods for controlling plant pathogenic bacteria and diseases caused thereby.

It is another object of the invention to provide effective, inexpensive, and environmentally appropriate compositions and methods for controlling plant diseases caused by plant pathogens and especially plant pathogenic bacteria.

These and other objects can be achieved by providing a method of protecting a plant part from infection by a plant pathogenic bacterium comprising the steps of:
 (a) providing a composition comprising an activity for inhibiting the growth of a plant pathogenic bacterium wherein the composition is made by:
  (i) providing a malted cereal grain,
  (ii) grinding the malted cereal grain into particles of an effective size for extraction of the activity therefrom with an aqueous solvent,
  (iii) adding an effective amount of an aqueous solvent to the particles to form a mixture and contacting the particles in the mixture with the aqueous solvent for a time sufficient for extraction of at least a portion of the activity from the particles into the aqueous solvent,
  (iv) fractionating the mixture such that the particles are substantially separated from the aqueous solvent containing the activity to form a clarified extract, and
  (v) concentrating the clarified extract to result in the composition comprising the activity for inhibiting growth of the plant pathogenic bacterium; and
 (b) contacting the plant part with an effective amount of the composition.

Preferably, the malted cereal grain is a member selected from the group consisting of malted barley, malted wheat, malted rye, and mixtures thereof. The plant pathogenic bacterium is preferably a bacterium from the genera Erwinia, Pseudomonas, Xanthomonas, Agrobacterium, or Clavibacter, and more preferably is a soft rot bacterium from the genum Erwinia. The filtered extract is preferably concentrated by lyophilization to obtain a dry composition. This dry composition can be applied as is to plant parts according to the present invention or can be reconstituted with an aqueous solvent to produce a wet formulation.

A method of making a composition for applying to a plant part to protect the plant part from infection by a plant pathogenic bacterium, the composition comprising an activity for inhibiting growth of the plant pathogenic bacterium, comprises the steps of:
 (a) providing a malted cereal grain;
 (b) grinding the malted cereal grain into particles of an effective size for extraction of the activity therefrom with an aqueous solvent;
 (c) adding an effective amount of an aqueous solvent to the particles to form a mixture and contacting the particles in the mixture with the aqueous solvent for a time sufficient for extraction of at least a portion of the activity from the particles into the aqueous solvent;
 (d) fractionating the mixture such that the particles are substantially separated from the aqueous solvent containing the activity to form a clarified extract; and
 (e) concentrating the clarified extract to result in the composition comprising the activity for inhibiting growth of the plant pathogenic bacterium.

A composition for applying to a plant part to protect the plant part from infection by a plant pathogenic bacterium comprises an activity for inhibiting growth of the plant pathogenic bacterium wherein the composition is made by a process comprising the steps of:
 (a) providing a malted cereal grain;
 (b) grinding the malted cereal grain into particles of an effective size for extraction of the activity therefrom with an aqueous solvent;
 (c) adding an effective amount of an aqueous solvent to the particles to form a mixture and contacting the particles in the mixture with the aqueous solvent for a time sufficient for extraction of at least a portion of the activity from the particles into the aqueous solvent;
 (d) fractionating the mixture such that the particles are substantially separated from the aqueous solvent containing the activity to form a clarified extract; and
 (e) concentrating the clarified extract to result in the composition comprising the activity for inhibiting growth of the plant pathogenic bacterium.

DETAILED DESCRIPTION

Before the present composition and method for controlling plant diseases are disclosed and described, it is to be understood that this invention is not limited to the particular configurations, process steps, and materials disclosed herein as such configurations, process steps, and materials may vary somewhat. It is also to be understood that the terminology employed herein is used for the purpose of describing particular embodiments only and is not intended to be limiting since the scope of the present invention will be limited only by the appended claims and equivalents thereof.

It must be noted that, as used in this specification and the appended claims, the singular forms "a," "an," and "the" include plural referents unless the context clearly dictates otherwise. Thus, for example, reference to a composition comprising "an activity" for inhibiting growth of a plant pathogenic bacterium includes reference to two or more of such activities, reference to "a solvent" includes reference to one or more of such solvents, and reference to "a bacterium" includes reference to two or more of such bacteria.

In describing and claiming the present invention, the following terminology will be used in accordance with the definitions set out below.

As used herein, "plant part" refers to a leaf, stem, root, fruit, seed, tuber, or the like that can be infected or invaded by a plant pathogenic bacterium.

As used herein, "plant pathogenic bacterium" refers to a bacterium capable of infecting and/or invading a plant part and causing disease therein. Plant pathogenic bacteria are preferably selected from the group consisting of Erwinia, Pseudomonas, Agrobacterium, Xanthomonas, and Clavibacter. Bacteria of the genus Erwinia are especially preferred plant pathogenic bacteria that are controlled according to the present invention. Soft rot bacteria, such as *Erwinia carotovora* ssp. *carotovora* or *Erwinia carotovora* ssp. *atroseptica*, are also preferred bacteria that can be controlled according to the present invention.

As used herein, "activity" means a component or components of malted cereal grains that can be extracted therefrom in an aqueous solvent and exerts an effect of inhibiting growth of a plant pathogenic bacterium when applied to a plant part.

As used herein, "malted cereal grain" or similar terms refers to a cereal grain that has been processed such that germination takes place and then the germinated seeds are heat treated. The malted grain described herein was malted by a commercial process and was obtained from Anheuser Busch. Briefly, the malting process involves washing raw grain by steeping in water for about 40 hours at 13°–15° C. The washed grain is then placed in bins at 15°–18° C. for about 4 days under controlled humidity conditions suitable for germination of the seeds. At the end of this incubation period, the grain has begun to germinate and is sometimes referred to as green malt. The germinating grain is then subjected to high temperature treatment comprising gradually increasing the temperature to about 65°–70° C. for about 24 hours for removal of water and arresting enzyme activity and further growth of the germinating grain. The resulting malted grain can then be stored or shipped for later use. As used herein, "green malt" is grain that is processed according to the method of making malted cereal grain through the germination or sprouting stage, but the following heat treatment is omitted. A 3-day green malt, e.g. for example, is obtained by germinating the grain for three days.

As used herein, "effective size" refers to a size of particles of ground malted grain that is effective for extraction of the activity for inhibiting the growth of selected plant pathogenic bacteria. It has been found that grinding malted grain into particles of about the size of particles of wheat flour is an effective size, but is suboptimal for extracting the activity. The activity can also be extracted from coarse particles of ground malted grain, but such coarse particles are also suboptimal, even though they are within the range of an effective size. It has been discovered that fine particles, i.e. particles smaller than coarse particles but larger than flour-sized particles, are optimal for extraction of the activity.

As used herein, "aqueous solvent" means a water-based solvent, including but not limited to tap water, distilled water, buffers, salt solutions, and the like. Water, either from the tap or distilled, is a preferred aqueous solvent.

As used herein, "effective amount" means an amount of aqueous solvent effective for extraction of the bacteria-inhibiting activity from particles of malted grain. Such an effective amount is preferably in the range of about 1–5 parts by weight of aqueous solvent per part by weight of malted grain particles, and more preferably about 2 parts by weight of aqueous solvent per part by weight of malted grain particles. "Effective amount" also means an amount of the composition of the present invention effective for achieving a selected result, i.e. inhibiting growth of plant pathogenic bacteria to a selected degree.

EXAMPLE 1

This example describes an illustrative method of preparing the composition according to the present invention. Malted barley was obtained from Anheuser Busch. The malted barley was then ground into particles that were subjectively referred to as a fine grind. Such particles were larger than grains of barley flour, but were not so large as to be considered coarse. The ground malted grain was then mixed with water in a weight ratio of about 1 part grain to 2 parts water. This mixture was then agitated at room temperature for about 24 hours with a shaker apparatus. Following this extraction in water, the mixture was filtered through a double layer of cheesecloth to remove relatively large particulates. The resulting filtrate had a milky appearance. This filtrate was then lyophilized to result in a powder, which can be used for application to seeds or other plant parts, or the powder can be rehydrated in an aqueous solvent for application to plant parts as a wet formulation, such as by spraying or dipping the plant parts in the composition.

EXAMPLE 2

In this example, the procedure of Example 1 was followed except that malted wheat was substituted for malted barley.

EXAMPLE 3

In this example, the procedure of Example 1 was followed except that malted rye was substituted for malted barley.

EXAMPLE 4

In this example, a composition prepared according to Example 1 was prepared in dry powder form, and then the powder composition was reconstituted with sterile distilled water at a weight ratio of 1:1. The isolate of *Erwinia carotovora* ssp. *atroseptica* used in this example was isolated from diseased potato tubers obtained from Kingston Produce, Idaho Falls, Id. This strain was differentiated from *E. carotovora* ssp. *carotovora* on crystal violet pectate medium according to Cupples & Kelman, 64 Phytopathology 464–75 (1974), hereby incorporated by reference. The *E. carotovora* ssp.. *atroseptica* isolate was grown on nutrient agar plates (Difco Manual) at 25° C., and was then serially diluted in sterile water for determining the concentration of colony forming units (CFU) by counting colonies on plates. An inoculum having a CFU concentration sufficient for forming a bacterial lawn was plated by spreading on nutrient agar plates, as is well known in the art of bacteriology as described, for example, in J. Miller, Experiments in Molecular Genetics, Cold Spring Harbor Laboratory, Cold Spring Harbor, N.Y. (1972), hereby incorporated by reference. Sterile filter disks (0.5 mm diameter; Fisher Scientific, Pittsburgh, Pa.) were placed on the surface of these plates, and a standard amount of the malted wheat extract was placed on each disk. Control plates were prepared identically except for the material placed on the disks. Control materials were: sterile distilled water, extract of raw barley grains, extract of whole malted barley kernels, extract of green malt incubated for 0 days, or extract of green malt incubated for 3 days. These control extracts were prepared according to the method of Example 1 except that the starting material, e.g. green malt, was substituted for malted grain. An extract of malted barley was also prepared from a coarse grind of malted barley in addition to the "fine grind" prepared according to the method of Example 1. A portion of the extract prepared from the fine grind of malted wheat was passed through a 0.2 μm filter to remove any bacterial cells or larger cells that may have been present. Plates were prepared with these control and experimental materials as described above. The plates were then placed in an incubator at 25° C. for overnight. The plates were then removed from the incubator and clearing zones around the disks were measured.

Figure 1:
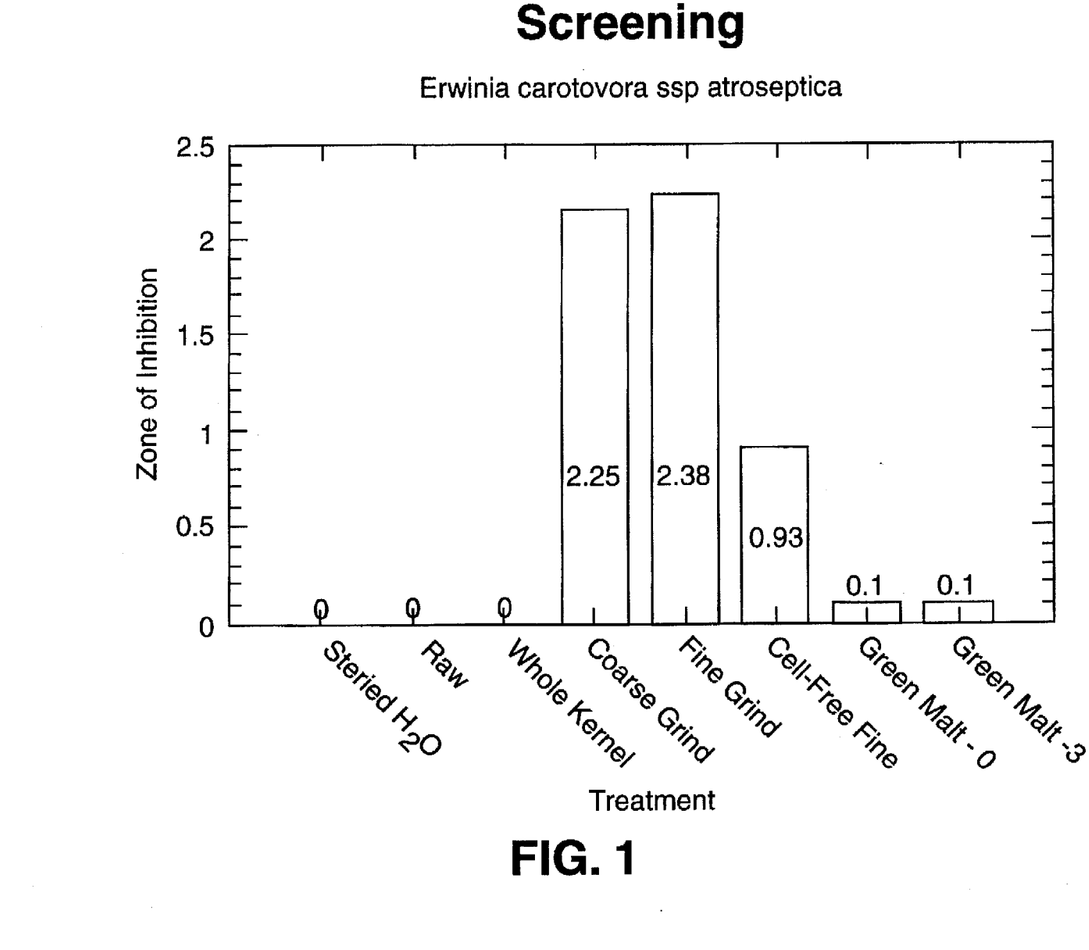
FIGS. 1 and 2 show in vitro inhibition of growth of *Erwinia carotovora* ssp. *atroseptica* and *Erwinia carotovora* ssp. *carotovora*, respectively, as measured by clearing zones (in mm) around filter disks containing sterile distilled water (sterile D H2O) or extracts of: raw barley grain (raw); whole malted barley kernel (whole kernel); coarsely ground malted barley (coarse grind); finely ground malted barley (fine grind); finely ground malted barley, wherein the extract was filter sterilized (cell-free fine); 0-day green malted barley (green malt-0); and 3-day green malted barley (green malt-3).
Figure 2:
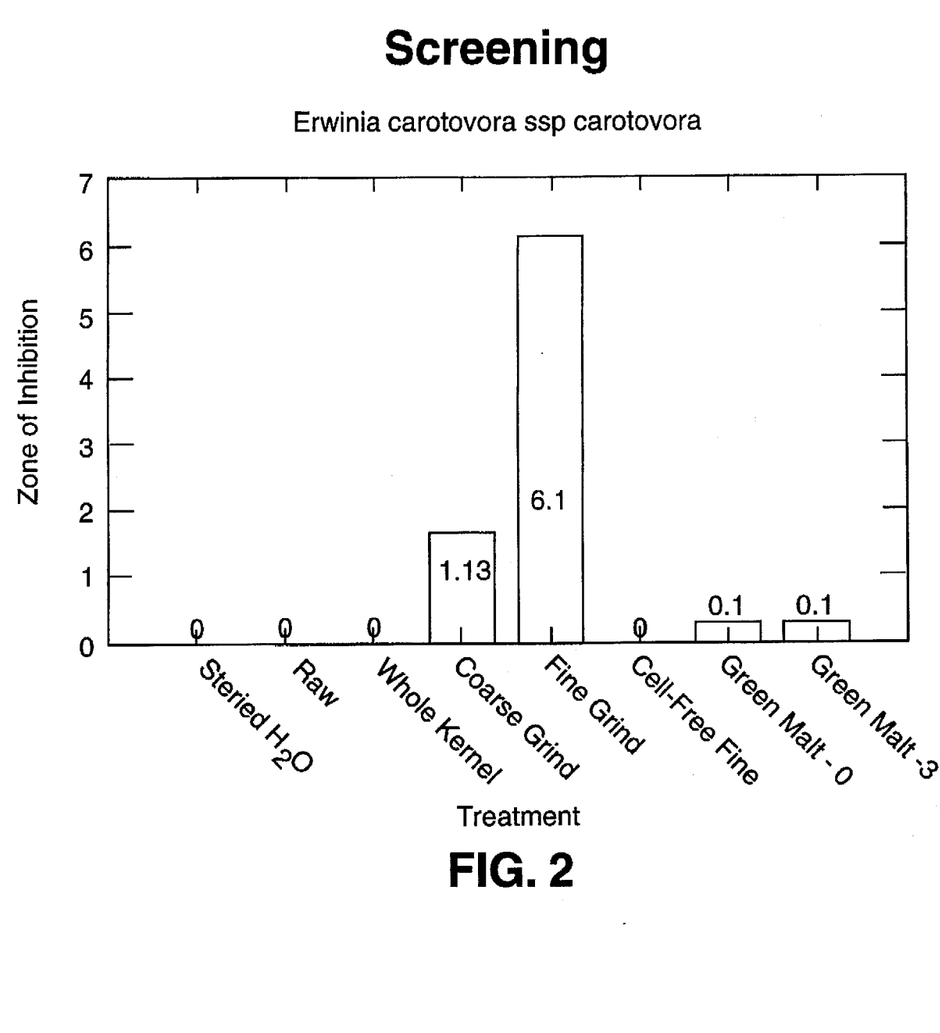
Figure 3:
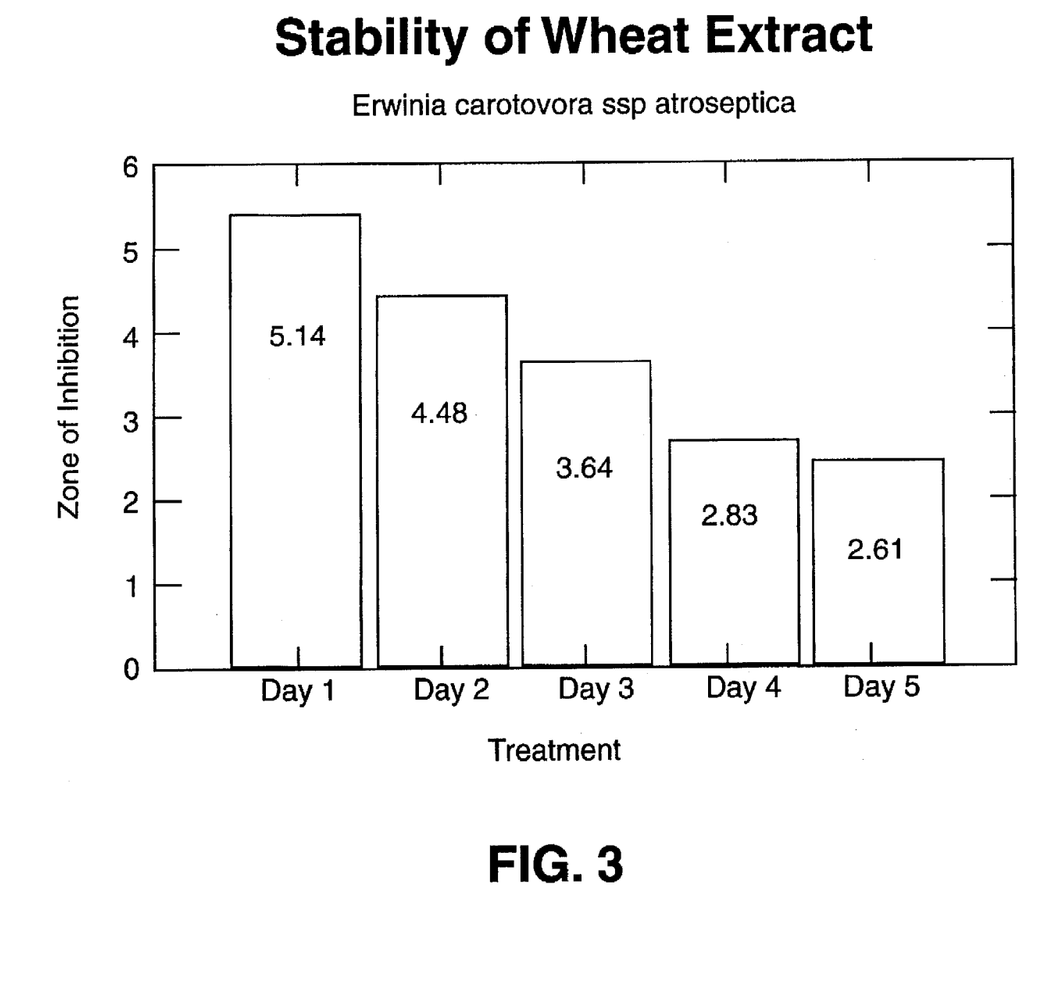
FIG. 3 shows in vitro inhibition of growth of *Erwinia carotovora* ssp. *atroseptica* as measured by clearing zones (in mm) around filter disks containing a standard amount of extract of malted wheat at days 1, 2, 3, 4, and 7 after plating.

FIG. 1 shows the results of this experiment. Values presented are the means of five disks on each of five plates. No clearing zones were observed around disks containing sterile distilled water or extracts from raw grain, whole malted kernels, 0-day green malt, or 3-day green malt. Significant clearing zones were observed around the disks containing extracts from the coarse and fine grinds of malted barley and from the filter-sterilized extract of finely ground malted barley. These results show that there is an activity in malted barley that is not present in raw grain, whole malted kernels, or green malt, that inhibits the growth of *E. carotovora* ssp. *atroseptica* in vitro. This activity is able to pass through a 0.2 μm filter, suggesting that it is not microbial per se, although it could be a product of microbial growth. The activity is diffusable in agar.

EXAMPLE 5

In this example, the procedure of Example 4 was followed except that the bacteria used were *Erwinia carotovora* ssp. *carotovora.* The isolate of *Erwinia carotovora* ssp. *carotovora* used in this example was isolated from diseased potato tubers obtained from Kingston Produce, Idaho Falls, Id. This strain was differentiated from *E. carotovora* ssp. *atroseptica* on crystal violet pectate medium according to Cupples & Kelman, 64 Phytopathology 464–75 (1974), as described above.

FIG. 2 shows the results of this experiment. No clearing zones were observed around disks containing sterile distilled water or extracts of raw grain, whole malted kernels, 0-day green malt, 3-day green malt, or the filter-sterilized extract of finely ground malted barley. Significant clearing zones were observed around filter disks containing finely ground and coarsely ground malted barley. The clearing zones around the disks containing extracts of finely ground malted barley were significantly larger than those around disks containing the coarsely ground malted barley, suggesting that extraction of the growth-inhibiting activity is more efficient from the finely ground malted barley as compared to the coarsely ground malted barley.

EXAMPLE 6

In this example, the procedure of Example 4 was followed with the exception that extract of malted wheat according to Example 2 was substituted for the extract of malted barley. The results were substantially similar to those presented in FIG. 1.

EXAMPLE 7

In this example, the procedure of Example 4 was followed with the exception that extract of malted rye according to Example 3 was substituted for the extract of malted barley. The results were substantially similar to those presented in FIG. 1.

EXAMPLE 8

In this example, the procedure of Example 4 was followed with the exception that plates were incubated for 7 days following plating, and clearing zones were measured 1, 2, 3, 4, and 7 days after plating. FIG. 3 shows the results of this experiment, wherein regrowth into the clearing zones is observed in days 2–7 following plating. This regrowth may be due to dilution of the activity responsible for inhibiting growth of the bacteria. However, the presence of clearing zones after 7 days of incubation suggests the activity responsible for inhibiting bacterial growth is stable for at least 7 days at 25° C.

EXAMPLE 9

In this example, the procedure of Example 8 was followed except that *Erwinia carotovora* ssp. *carotovora* was substituted for *E. carotovora* ssp. *atroseptica.* The results were substantially similar to those shown in FIG. 3.

EXAMPLE 10

In this example, a dry powder extract was prepared from malted wheat according to the procedure of Example 1. A portion of the powder was mixed with sterile water in equal parts by weight to result in a wet formulation. A 2 cm diameter cork borer was used to cut cores from potato tubers, and these cores were sliced into disks about 6 mm thick. These disks were then treated with various control or experimental treatments, and were then incubated in petri dishes for 4.5 days. Following incubation, the disks were weighed, washed with water to remove loose tissue, and weighed again. The percent weight loss was determined by dividing the second weight by the first weight and multiplying the result by 100.

The treatments involved spraying the disks (except uninoculated controls) with $10^8$ cells/ml of *Erwinia carotovora* ssp. *carotovora* and then treating with powdered or reconstituted malted wheat extract. Disks treated with powdered extract were treated at the rates of 1 lb/cw, 2 lb/cw, and an undefined amount that was as much as would adhere to each disk. Other disks were dipped in the wet formulation (equal parts by weight of powdered extract of malted wheat and sterile water). Control disks were inoculated but not treated with extract of malted wheat.

Figure 4:
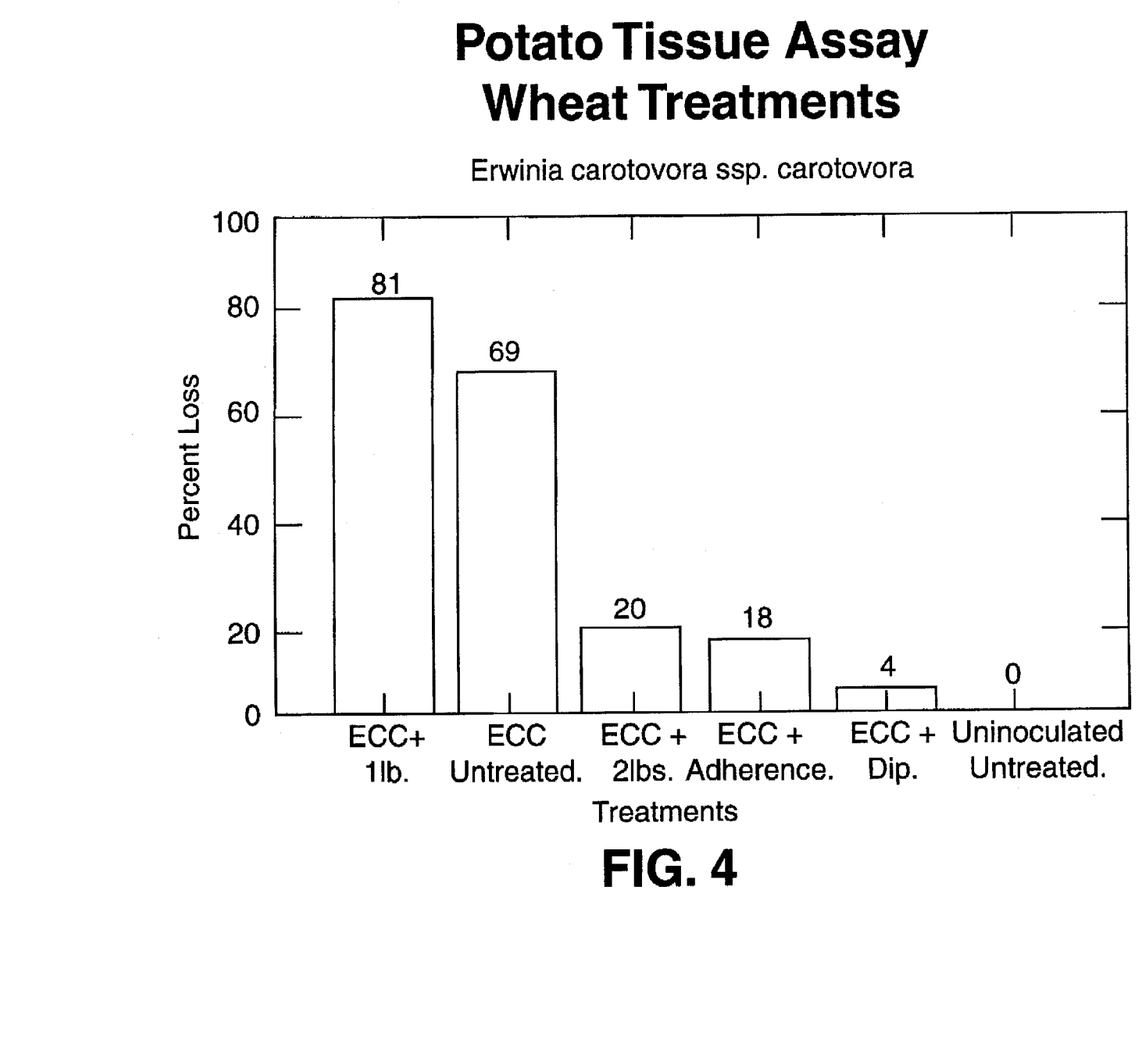
FIGS. 4 and 5 show the percent weight loss from potato disks inoculated with $10^8$ cells/ml of *Erwinia carotovora* ssp. *carotovora* or *Erwinia carotovora* ssp. *atroseptica*, respectively, and treated with extract of malted wheat as follows: inoculated and treated at 1 lb/cw (ECC+1 lb); inoculated and untreated (ECC Untreated); inoculated and treated at 2 lb/cw (ECC+2 lbs); inoculated and treated with as much powdered extract as would adhere to the potato disks (ECC+Adherence); inoculated and dipped in liquid extract (ECC+Dip); uninoculated and untreated control (Uninoculated Untreated).

FIG. 4 shows that treatment of the potato disks with extract of malted wheat at a rate of 2 lb/cw or as much as would adhere to the disks or dipping in a wet formulation of the extract resulted in significant reductions in weight loss due to soft rot. In this experiment, treatment with powdered extract at a rate of 1 lb/cw resulted in more weight loss than the inoculated, untreated control.

EXAMPLE 11

Figure 5:
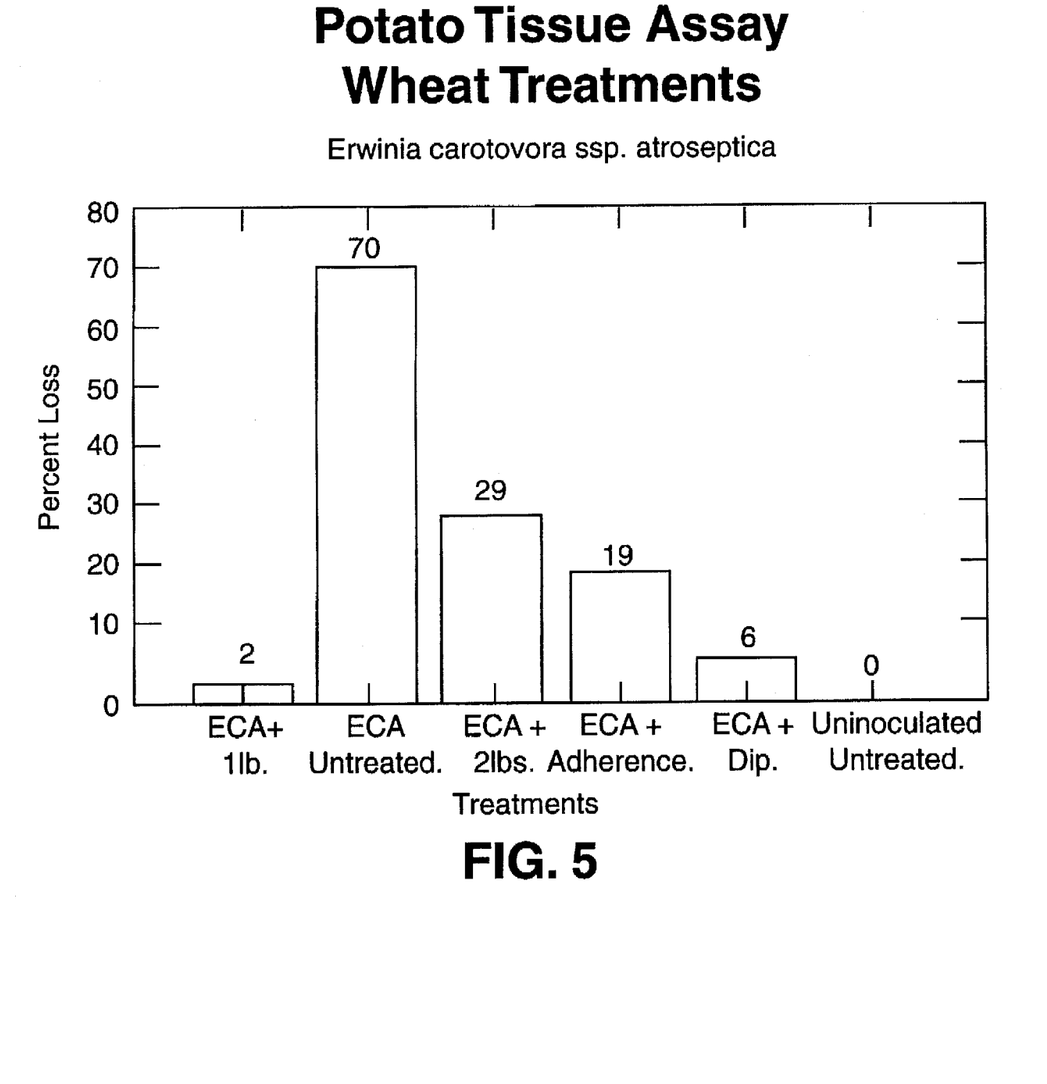

In this example, the procedure of Example 10 was followed except that *Erwinia carotovora* ssp. *atroseptica* was substituted for *Erwinia carotovora* ssp. *carotovora*. FIG. 5 shows the results of this experiment, wherein all of the treatments with extract of malted wheat resulted in significant reductions in loss of tissue due to soft rot.

EXAMPLE 12

In this example, potato seed pieces were quartered with a knife and then immediately sprayed with $10^8$ cell/ml of *Erwinia caratovara* ssp. *atroseptica*. Following inoculation, the seed pieces were placed in a plastic bag and shaken with a dry formulation of extract of malted barley, prepared according to Example 2, and then placed in controlled-humidity chambers for incubation at 15° C. Following incubation for 6 days, the seed pieces were removed from the chambers, weighed, washed to remove loose tissue, and weighed again. The weight loss in grams was recorded. The treatments included powdered extract of malted barley at a rate of 1 lb/cw, a mixture of 75% by weight of powdered extract of malted barley and 25% by weight of bark carrier, and a mixture of 50% by weight of powdered extract of malted barley and 50% by weight of bark carrier.

Figure 6:
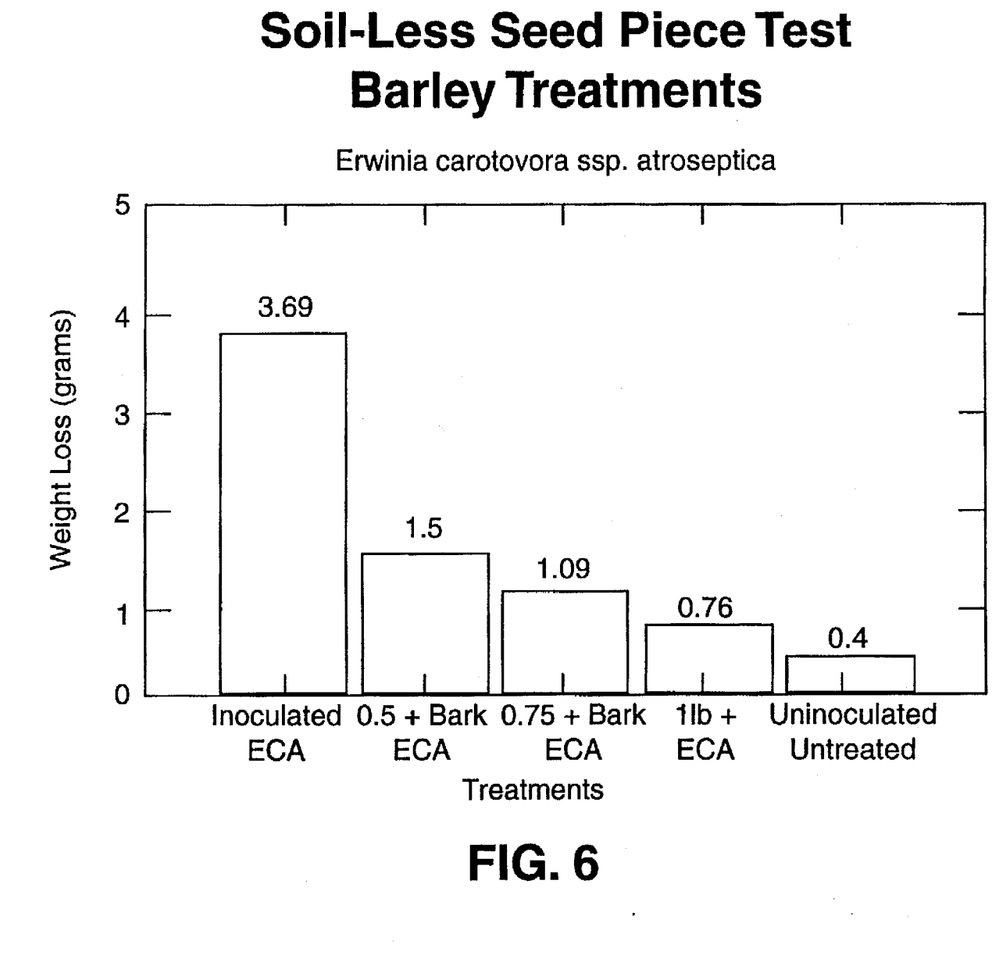
FIG. 6 shows the amount of weight loss in grams in quartered potato seed pieces inoculated with *Erwinia carotovora* ssp. *atroseptica* and treated as follows: inoculated and untreated (Inoculated ECA); inoculated and treated with 50% (w/w) powdered extract of malted barley and 50% (w/w) bark carrier (0.5+Bark ECA); inoculated and treated with 75% (w/w) powdered extract of malted barley and 25% (w/w) bark carrier (0.75+Bark ECA); inoculated and treated with 1 lb/cw of powdered extract of malted barley (1 lb+ECA); and uninoculated and untreated (Uninoculated Untreated).

FIG. 6 shows that treatment of inculated seed pieces with powdered extract of malted barley significantly reduced the amount of tissue loss due to soft rot. The treatments containing the bark carrier were not as effective in protecting against weight loss due to soft rot, but were significantly better than no treatment at all.

EXAMPLE 13

In this example, the procedure of Example 12 was followed except that *Erwinia carotovora* ssp. *carotovora* was substituted for *Erwinia carotovora* ssp. *atroseptica*. The results were substantially similar to those of FIG. 6.

EXAMPLE 14

In this example, the procedure of Example 12 was followed except that the extract used was from malted wheat instead of malted barley. The results were substantially similar to those of FIG. 6.

EXAMPLE 15

In this example, the procedure of Example 13 was followed except that the extract used was from malted wheat instead of malted barley. The results were substantially similar to those of FIG. 6.

EXAMPLE 16

In this example, the procedure of Example 4 was followed except that *Erwinia amylovora*, the etiological agent of fireblight of pear and other fruits, was substituted for *Erwinia carotovora*. The results were substantially similar to those of Example 4.

Application to Plant Parts

The composition of the present invention can be applied to plant parts as a dry material or as a wet formulation. As a dry material, the composition can be applied directly to the plant parts to be protected, for example potato tubers. The dry material can also be applied to leaves, fruits, and the like by dusting. The wet formulation can be applied by spraying onto the plant parts to be protected, or the plant parts can be dipped in the wet formulation, for example by dipping tubers or fruits.

I claim:

1. A method of protecting a plant part from infection by a plant pathogenic bacterium comprising the steps of:

(a) providing a composition comprising an activity for inhibiting the growth of a plant pathogenic bacterium wherein said composition is made by:
 (i) providing a malted cereal grain,
 (ii) grinding said malted cereal grain into particles of an effective size for extraction of said activity therefrom with an aqueous solvent,
 (iii) adding an effective amount of an aqueous solvent to said particles to form a mixture and contacting said particles in said mixture with said aqueous solvent for a time sufficient for extraction of at least a portion of said activity from said particles into said aqueous solvent,
 (iv) fractionating said mixture such that said particles are substantially separated from said aqueous solvent containing said activity to form a clarified extract, and
 (v) concentrating said clarified extract to result in said composition comprising said activity for inhibiting growth of said plant pathogenic bacterium; and
(b) contacting said plant part with an effective amount of said composition.

2. The method of claim 1 wherein said malted cereal grain is a member selected from the group consisting of malted barley, malted wheat, malted rye, and mixtures thereof.

3. The method of claim 1 wherein said plant part is a potato seed piece.

4. The method of claim 1 wherein said concentrating comprises lyophilizing said clarified extract to obtain a dry composition.

5. The method of claim 4 further comprising reconstituting said dry composition by adding an effective amount of a second aqueous solvent thereto.

6. The method of claim 1 wherein said plant pathogenic bacterium is a soft rot bacterium.

7. The method of claim 6 wherein said soft rot bacterium is a member selected from the genus Erwinia.

8. A method of making a composition for applying to a plant part to protect said plant part from infection by a plant pathogenic bacterium, said composition comprising an activity for inhibiting growth of said plant pathogenic bacterium, comprising the steps of:

(a) providing a malted cereal grain;
(b) grinding said malted cereal grain into particles of an effective size for extraction of said activity therefrom with an aqueous solvent;

(c) adding an effective amount of an aqueous solvent to said particles to form a mixture and contacting said particles in said mixture with said aqueous solvent for a time sufficient for extraction of at least a portion of said activity from said particles into said aqueous solvent;

(d) fractionating said mixture such that said particles are substantially separated from said aqueous solvent containing said activity to form a clarified extract; and (e) concentrating said clarified extract to result in said composition comprising said activity for inhibiting growth of said soft rot organism.

9. The method of claim 8 wherein said malted cereal grain is a member selected from the group consisting of malted barley, malted wheat, malted rye, and mixtures thereof.

10. The method of claim 8 wherein said concentrating comprises lyophilizing said clarified extract to obtain a dry composition.

11. The method of claim 10 further comprising reconstituting said dry composition by adding an effective amount of a second aqueous solvent thereto.

12. The method of claim 8 wherein said plant pathogenic bacterium is a soft rot bacterium.

13. The method of claim 12 wherein said plant pathogenic bacterium is a member selected from the genus Erwinia.

14. A composition comprising an activity for inhibiting growth of a plant pathogenic bacterium for applying to a plant part to protect said plant part from infection by said plant pathogenic bacterium, wherein said composition is made by a process comprising the steps of:

(a) providing a malted cereal grain;

(b) grinding said malted cereal grain into particles of an effective size for extraction of said activity therefrom with an aqueous solvent;

(c) adding an effective amount of an aqueous solvent to said particles to form a mixture and contacting said particles in said mixture with said aqueous solvent for a time sufficient for extraction of at least a portion of said activity from said particles into said aqueous solvent;

(d) fractionating said mixture such that said particles are substantially separated from said aqueous solvent containing said activity to form a clarified extract; and (e) concentrating said clarified extract to result in said composition comprising said activity for inhibiting growth of said plant pathogenic bacterium.

15. The composition of claim 14 wherein said malted cereal grain
is a member selected from the group consisting of malted barley, malted wheat, malted rye, and mixtures thereof.

16. The composition of claim 14 wherein said concentrating comprises lyophilizing said clarified extract to obtain a dry composition.

17. The composition of claim 16 further comprising reconstituting said dry composition by adding an effective amount of a second aqueous solvent thereto.

18. The composition of claim 15 wherein said plant pathogenic bacterium is a soft rot bacterium.

19. The composition of claim 18 wherein said soft rot bacterium is a member selected from the genus Erwinia.

* * * * *